(12) United States Patent
Kim et al.

(10) Patent No.: US 9,464,042 B2
(45) Date of Patent: Oct. 11, 2016

(54) BIGUANIDE DERIVATIVE, PREPARATION METHOD THEREOF, AND PHARMACEUTICAL COMPOSITION CONTAINING SAME AS AN ACTIVE INGREDIENT

(71) Applicant: IMMUNOMET THERAPEUTICS INC., Cambridge, MA (US)

(72) Inventors: Sung Wuk Kim, Gyeonggi-do (KR); Sung Soo Jun, Gyeonggi-do (KR); Chang Hee Min, Seoul (KR); Se Hwan Park, Daejeon (KR); Yong Eun Kim, Daejeon (KR); Duck Kim, Daegu (KR); Ji Sun Lee, Daejeon (KR); Ju Hoon Oh, Gangwon-do (KR)

(73) Assignee: IMMUNOMET THERAPEUTICS INC., Cambridge, MA (US)

( * ) Notice: Subject to any disclaimer, the term of this patent is extended or adjusted under 35 U.S.C. 154(b) by 0 days.

(21) Appl. No.: 14/847,692

(22) Filed: Sep. 8, 2015

(65) Prior Publication Data

US 2015/0376123 A1 Dec. 31, 2015

Related U.S. Application Data

(62) Division of application No. 13/520,905, filed as application No. PCT/KR2011/000098 on Jan. 6, 2011, now Pat. No. 9,133,110.

(30) Foreign Application Priority Data

Jan. 6, 2010 (KR) .................. 10-2010-0001021
Jan. 6, 2011 (KR) .................. 10-2011-0001442

(51) Int. Cl.

| | | |
|---|---|---|
| A61K 31/44 | (2006.01) | |
| C07C 279/16 | (2006.01) | |
| C07C 279/26 | (2006.01) | |
| C07C 277/04 | (2006.01) | |
| C07C 279/04 | (2006.01) | |
| C07C 279/06 | (2006.01) | |
| C07C 279/08 | (2006.01) | |
| C07C 279/18 | (2006.01) | |
| C07D 213/38 | (2006.01) | |
| C07D 307/52 | (2006.01) | |
| C07D 317/58 | (2006.01) | |
| C07D 333/20 | (2006.01) | |

(52) U.S. Cl.
CPC .......... *C07C 279/16* (2013.01); *C07C 277/04* (2013.01); *C07C 279/04* (2013.01); *C07C 279/06* (2013.01); *C07C 279/08* (2013.01); *C07C 279/18* (2013.01); *C07C 279/26* (2013.01); *C07D 213/38* (2013.01); *C07D 307/52* (2013.01); *C07D 317/58* (2013.01); *C07D 333/20* (2013.01); *C07C 2101/08* (2013.01); *C07C 2101/14* (2013.01); *C07C 2101/18* (2013.01); *C07C 2103/74* (2013.01)

(58) Field of Classification Search
CPC .................................................... C07C 279/16
USPC .......................................................... 514/357
See application file for complete search history.

(56) References Cited

U.S. PATENT DOCUMENTS

| | | |
|---|---|---|
| 3,960,949 A | 6/1976 | Ahrens et al. |
| 7,199,159 B2 | 4/2007 | Potier et al. |
| 8,642,647 B2 | 2/2014 | Kim et al. |
| 8,648,111 B2 | 2/2014 | Kim et al. |

FOREIGN PATENT DOCUMENTS

| | | |
|---|---|---|
| KR | 10-2003-0029050 | 4/2003 |
| WO | WO 01-91696 | 12/2001 |
| WO | WO 2004/026241 | 4/2004 |
| WO | WO 2009-113092 | 9/2009 |
| WO | WO2010/044581 | 4/2010 |
| WO | WO 2010/044582 | 4/2010 |

OTHER PUBLICATIONS

Sporn et al. The American Journal of Medicine, Jun. 1981, 70(6), 1231-1236.*
Camacho et al. Breast Cancer Research (2015.*
Freshney (Culture of Animal Cells, A Manual of Basic Technique, Alan R. Liss, Inc., 1983, New York, p4).*
Simeone in Cecil Textbook of Medicine, 20th ed. J.C. Bennett. Philadelphia: WB Saunders Co., 1996.*
Carrington et al., "Synthetic Antimalarials, Part XLIX. The Structure and Synthesis of the Dihydrotriazine Metabolite of Proguanil", Journal of Chem. Soc., 1954, pp. 1017-1031.
International Search Report mailed Sep. 2, 2011 for International Patent Application No. PCT/KR2011/00098.
Paul, S. P. "Synthesis of Biguanides as Potential Hypolycaemic Agents: Part IV-Structure-Activity Relationship", Indian Journal of Chemistry (1963), V. 1:218-220.

(Continued)

*Primary Examiner* — Nizal Chandrakumar
(74) *Attorney, Agent, or Firm* — Swanson & Bratschun, L.L.C.

(57) ABSTRACT

A biguanide derivative compound with N4-N5 substitution, which is represented by Formula 1, or a pharmaceutically acceptable salt thereof, a method of preparing the same, and a pharmaceutical composition containing the same as an active ingredient are provided. The biguanide derivative may exhibit excellent effect on activation of AMPK and inhibition of cancer cell proliferation in a low dose, compared with conventional drugs, and thus, may be useful to treat diabetes mellitus, obesity, hyperlipidemia, hypercholesterolemia, fatty liver, coronary artery disease, osteoporosis, polycystic ovarian syndrome, metabolic syndrome, cancer, etc.

3 Claims, No Drawings

(56) References Cited

OTHER PUBLICATIONS

Buzzai et al. (2007) "T=Systemic Treatment with the Antidiabetic Drug Metformin Selectively Impairs p53-Deficient Tumor Cell Growth" Cancer Research V. 67: 6745-6752.

Chinese Office Action for CN Patent Application No. 201180005604.X, dated May 29, 2013, 13 pages.
E. C. Franklin in the Journal of the American Chemical Society "The Ammono Carbonic Acids" 1922, V. 44: 486-509.

* cited by examiner

BIGUANIDE DERIVATIVE, PREPARATION METHOD THEREOF, AND PHARMACEUTICAL COMPOSITION CONTAINING SAME AS AN ACTIVE INGREDIENT

RELATED APPLICATIONS

This application is a divisional application of U.S. patent Ser. No. 13/520,905, filed on Jul. 6, 2012, entitled "BIGUANIDE DERIVATIVE, PREPARATION METHOD THEREOF, AND PHARMACEUTICAL COMPOSITION CONTAINING SAME AS AN ACTIVE INGREDIENT", which is a 35 U.S.C. §371 national phase application of PCT/KR2011/000098 (WO 2011/083999), filed on Jan. 6, 2011, entitled "BIGUANIDE DERIVATIVE, PREPARATION METHOD THEREOF, AND PHARMACEUTICAL COMPOSITION CONTAINING SAME AS AN ACTIVE INGREDIENT", which application Korean Application No. 10-2011-0001442, filed Jan. 6, 2011 and Korean Application No. 10-2010-0001021, filed Jan. 6, 2010

TECHNICAL FIELD

The present invention relates to a biguanide derivative exhibiting excellent effects on activation of 5'-AMP-activated protein kinase (AMPK) and inhibition of cancer cell proliferation in a low dose compared with conventional drugs, a method of preparing the same, and a pharmaceutical composition containing the same as an active ingredient.

BACKGROUND ART

Diabetes mellitus, a disease characterized by continuous hyperglycemia, is a disorder that affects the metabolization of carbohydrates and lipids. It is a disease aggravated by bloodstream disorders caused by hyperglycemia and systemic complications caused by decreased utilization of sugar. Diabetes mellitus is induced by insulin deficiency or insulin resistance, and diabetes mellitus that occurs due to insulin resistance is called type 2 diabetes mellitus.

Type 2 diabetes mellitus is caused by a malfunctioning of insulin in delivering sugar into cells due to the reduction in the number of insulin receptors or defects in the signal transduction system through a receptor, a condition known as insulin resistance. Type 2 diabetes mellitus directly destroys blood vessels due to hyperinsulinemia and aggravates metabolic syndrome.

Many kinds of drugs have been used to treat type 2 diabetes mellitus. However, except for biguanide metformin, drugs are only partly effective in lowering blood sugar and are not sufficient in effectively preventing serious complications such as loss of sight, paralysis, apoplexy, renal failure, peripheral neuropathy, foot ulcer, etc. For example, a sulfonylurea-based drug forces insulin to be secreted from the pancreas to lower blood sugar. The medicinal effects of the sulfonylurea-based drug disappear immediately. Also, the sulfonylurea-based drug induces an abnormal lipid metabolism, thereby resulting in arteriosclerosis, weight gain, and brain damage caused by hypoglycemia. In addition, a glitazone-based drug is used in combination with metformin because it resolves the problem of insulin resistance in adipose tissues but has a side effect of destroying the retinal vessels. For these reasons, use of the glitazone-based drug requires special attention.

Metformin does not induce hypoglycemia, but it overcomes the problem of insulin resistance in adipose tissues, liver tissues and muscle tissues, and it functions to drastically lower blood sugar and decrease the level of glycosylated hemoglobin.

In addition, metformin is known to activate an AMP-activated protein kinase that physiologically controlls carbohydrate and lipid metabolism and is also reported to decrease blood sugar level, improve lipid condition, and normalize menstrual irregularity, ovulation and pregnancy. Moreover, it has been proven that when metformin is used to treat p53 gene-deficient cancer cells, metformin activates an AMPK enzyme of the cancer cells and changes the metabolic energy pathway, and therefore, the cancer cells finally die [Monica Buzzai et al., Systemic Treatment with the Antidiabetic drug Metformin Selectively Impairs p53-Deficient Tumor Cell Growth, Cancer Res 2007; 67:(14)] since they cannot adjust to the changed metabolic pathway, In addition, Josie M M Evans reported a study concluding that a type 2 diabetes mellitus patient administered with metformin has a lower risk of cancer than a patient who has not been administered with metformin [Josie M M, Evans et al. BMJ. 2005, 330, 1304-1305]. Moreover, Samantha L. Browker reported that patients with type 2 diabetes mellitus who take metformin orally have a lower cancer mortality rate than patients who take sulfonylurea orally or are administered with insulin [Samantha L et al., Diabetes mellitus Care. 2006, 29, 254-258].

There is an increasing amount of clinical evidence indicating that a cancer stem cell is involved in the recurrence and metastasis of cancer. The content of cancer stem cells in a tumor tissue is 0.2% or less, but the cancer stem cells may not be removed by conventional anticancer chemotherapy. Metformin has an anticancer effect on cancer stem cells and excellent tolerability. In recent research relating to metformin, it has been reported that when doxorubicin, which is an anticancer drug, is administered alone, there is little change in cancer stem cells, but when administered together with metformin, it removes cancer stem cells [Heather A. Hirsch et al., Metformin Selectively Targets Cancer Stem Cells, and Acts Together with Chemotherapy to Block Tumor Growth and Prolong Remission, Cancer Res 2009; 69: (19) Oct. 1, 2009].

However, metformin is generally administered three times a day, and a single dose is approximately 500 mg or more. Thus, to prepare metformin as a sustained-released tablet to be administered once a day, the tablet should contain approximately 1,500 mg or more of metformin, but such a tablet is too large for most patients to take. In addition, since extended release formulation available in the current market contains only approximately 750 mg of metformin, at least two tablets should be taken. For these reasons, a metformin-based substance exhibiting better pharmacological action than conventional metformin and having improved physiochemical characteristics is needed.

DISCLOSURE

Technical Problem

The present invention is directed to provide a novel biguanide derivative or a pharmaceutically acceptable salt thereof, which exhibits excellent effects on activation of AMPK and inhibition of cancer cell proliferation in a low dose, compared with conventional drugs, and a method of preparing the same.

The present invention is also directed to provide a pharmaceutical composition containing the above-mentioned compound as an active ingredient to treat diabetes mellitus, obesity, hyperlipidemia, hypercholesterolemia, fatty liver, coronary artery disease, osteoporosis, polycystic ovarian syndrome, metabolic syndrome, cancer, etc.

Technical Solution

One aspect of the present invention provides a biguanide derivative compound with N4-N5 substitution, represented by Formula 1, or a pharmaceutically acceptable salt thereof.

[Formula 1]

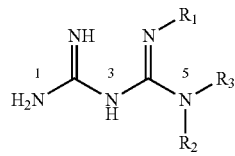

In Formula 1, $R_1$, $R_2$, and $R_3$ are independently hydrogen or a non-hydrogen substituent selected from the group consisting of $C_{1-12}$ alkyl unsubstituted or substituted with at least one non-hydrogen substituent selected from the group consisting of $C_{5-12}$ aryl, $C_{5-12}$ heteroaryl, $C_{3-10}$ cycloalkyl, hydroxyl and halogen; $C_{1-12}$ alkoxy; $C_{2-4}$ alkenyl; $C_{3-10}$ cycloalkyl; hydroxyl; halogen; $C_{5-12}$ aryl; and $C_{5-12}$ heteroaryl, and the aryl and heteroaryl are unsubstituted or substituted with at least one non-hydrogen substituent selected from the group consisting of $C_{1-4}$ alkyl, $C_{1-4}$ alkoxy, hydroxyl and halogen. Here, the non-hydrogen substituent for the aryl and heteroaryl may further be substituted with $C_{1-4}$ alkyl, $C_{1-4}$ alkoxy, hydroxyl or halogen.

A "substituted" group used herein is a group in which at least one hydrogen atom is replaced with at least one non-hydrogen atom group, provided that the group has to satisfy a requirement of valence and generate a chemically stable compound from the substitution. In the specification, unless explicitly described as "unsubstituted," it should be understood that all of substituents will be substituted or unsubstituted. The $R_1$ to $R_3$ substituents on the biguanide according to the present invention may each be substituted again with at least one of the above-defined substituents.

"Alkyl" refers to linear and branched saturated hydrocarbons, generally having a specified number of carbon atoms (for example, 1 to 12 carbon atoms). Examples of the alkyl group include, without limitation, methyl, ethyl, n-propyl, isopropyl, n-butyl, sec-butyl, isobutyl, tert-butyl, n-pentyl, n-hexyl, n-heptyl, etc. "Alkenyl" refers to an alkyl group containing at least one double bond. Examples of the alkenyl group include, without limitation, ethenyl, 1-propen-1-yl, 1-propen-2-yl, 2-propen-1-yl, allyl, etc. The alkyl or alkenyl may be attached to a parent group or a substrate at any ring atom, unless such attachment would violate valence requirements. Likewise, the alkyl or alkenyl group may include at least one non-hydrogen substituent unless such substitution would violate valence requirements.

"Cycloalkyl" refers to saturated monocyclic and polycyclic hydrocarbon rings, generally having a specified number of carbon atoms that include the ring (for example, $C_{3-10}$ cycloalkyl refers to a cycloalkyl group having 3, 4, 5, 6, 7, 8, 9, or 10 carbon atoms as ring members). The cycloalkyl may be attached to a parent or substrate at any ring atom, unless such attachment would violate valence requirements. Likewise, the cycloalkyl group may include at least one non-hydrogen substituent unless such substitution would violate valence requirements.

"Aryl" refers to monovalent and bivalent aromatic groups, respectively including 5- and 6-membered monocyclic aromatic groups and "heteroaryl" refers to monovalent and bivalent aromatic groups, respectively including 5- and 6-membered monocyclic aromatic groups that contain 1 to 4 heteroatoms independently selected from nitrogen, oxygen and sulfur. Examples of the monocyclic aryl group and heteroaryl group include, without limitation, phenyl, pyridinyl, furanyl, pyrrolyl, thiopheneyl, thiazolyl, isothiazolyl, imidazolyl, triazolyl, tetrazolyl, pyrazolyl, oxazolyl, isoxazolyl, pyrazinyl, pyridazinyl, pyrimidinyl, etc. The aryl and heteroaryl groups also include bicyclic groups, tricyclic groups, etc., including fused 5- and 6-membered rings as described above. Examples of the polycyclic aryl and heteroaryl groups include, without limitation, isoquinolinyl, naphthyl, biphenyl, anthracenyl, pyrenyl, carbazolyl, benzoxazolyl, benzodioxazolyl, benzothiazolyl, benzoimidazolyl, benzothiopheneyl, quinolinyl, indolyl, benzofuranyl, purinyl, indolizinyl, etc. The aryl and heteroaryl groups may be attached to a parent group or to a substrate at any ring atom, unless such attachment would violate valence requirements. Likewise, the aryl and heteroaryl groups may include at least one non-hydrogen substituent unless such substitution would violate valence requirements. Non-hydrogen substituents of the acryl and heteroaryl groups may also be substituted with additional non-hydrogen substituents.

"Alkoxy" refers to alkyl-O—. Here, the alkyl is defined above. Examples of the alkoxy group include, without limitation, methoxy, ethoxy, etc. The alkoxy may be attached to a parent group or to a substrate at any ring atom, unless such attachment would violate valence requirements. Likewise, the alkoxy group may include at least one non-hydrogen substituent unless such substitution would violate valence requirements.

"Hydroxyl" refers to —OH, "halogen" refers to fluoro, chloro, bromo, and iodo.

In the compound of Formula 1 of the present invention, $R_1$, $R_2$, and $R_3$ may be independently hydrogen or a non-hydrogen substituent selected from the group consisting of $C_{1-12}$ alkyl; $C_{2-4}$ alkenyl; $C_{3-10}$ cycloalkyl; $C_{5-12}$ aryl; and $C_{5-12}$ heteroaryl.

Here, the $C_{1-12}$ alkyl may be a linear or branched $C_{1-12}$ alkyl unsubstituted or substituted with at least one non-hydrogen substituent. When the alkyl is substituted with a non-hydrogen substituent, the alkyl may be, but is not limited to, a linear or branched alkyl having 1 to 6 carbon atoms. Here, non-hydrogen substituents for the alkyl may be selected from the group consisting of $C_{5-12}$ aryl, $C_{5-12}$ heteroaryl, $C_{3-10}$ cycloalkyl, hydroxyl and halogen, but the present invention is not limited thereto. The non-hydrogen substituents may also be further substituted or unsubstituted. For example, the aryl and heteroaryl may be unsubstituted or substituted with at least one non-hydrogen substituent selected from the group consisting of $C_{1-4}$ alkyl, $C_{1-4}$ alkoxy, hydroxyl and halogen. Here, the non-hydrogen substituent for the aryl and heteroaryl may further be substituted with $C_{1-4}$ alkyl, $C_{1-4}$ alkoxy, hydroxyl or halogen.

In one embodiment, $R_1$, $R_2$, and $R_3$ are independently hydrogen or a non-hydrogen substituent selected from the group consisting of unsubstituted $C_{1-7}$ alkyl; $C_{1-6}$ alkyl substituted with at least one non-hydrogen substituent selected from the group consisting of $C_{5-12}$ aryl, $C_{5-12}$ heteroaryl, $C_{3-10}$ cycloalkyl, hydroxyl and halogen; $C_{1-6}$ alkoxy; unsubstituted $C_{2-4}$ alkenyl; unsubstituted $C_{3-10}$ cycloalkyl; hydroxyl; halogen; $C_{5-12}$ aryl; and $C_{5-12}$ heteroaryl, the aryl and heteroaryl may be unsubstituted or substituted with at least one non-hydrogen substituent selected from the group consisting of $C_{1-4}$ alkyl, $C_{1-4}$ alkyl substituted with halogen, $C_{1-4}$ alkoxy, hydroxyl and halogen. Here, the non-hydrogen substituent for the aryl and heteroaryl may further be substituted with $C_{1-4}$ alkyl, $C_{1-4}$ alkoxy, hydroxyl or halogen.

In one embodiment, $R_1$ is a non-hydrogen substituent selected from the group consisting of unsubstituted $C_{1-7}$ alkyl; $C_{1-6}$ alkyl substituted with $C_{5-12}$ aryl or $C_{5-12}$ heteroaryl; unsubstituted $C_{2-4}$ alkenyl; unsubstituted $C_{3-10}$ cycloalkyl; $C_{5-12}$ aryl; and $C_{5-12}$ heteroaryl, $R_2$ is unsubstituted $C_{1-7}$ alkyl; $C_{1-6}$ alkyl substituted with $C_{5-12}$ aryl; $C_{5-12}$ heteroaryl; or hydrogen, and $R_3$ is a non-hydrogen substituent selected from the group consisting of unsubstituted $C_{1-7}$ alkyl; $C_{1-6}$ alkyl substituted with $C_{5-12}$ aryl or $C_{5-12}$ heteroaryl; unsubstituted $C_{3-10}$ cycloalkyl; $C_{5-12}$ aryl; and $C_{5-12}$ heteroaryl, the aryl and heteroaryl may be unsubstituted or substituted with at least one non-hydrogen substituent selected from the group consisting of $C_{1-4}$ alkyl, $C_{1-4}$ alkoxy, hydroxyl and halogen. Here, the non-hydrogen substituent for the aryl and heteroaryl may further be substituted with $C_{1-4}$ alkyl, $C_{1-4}$ alkoxy, hydroxyl or halogen.

In one embodiment, $R_1$ is a non-hydrogen substituent selected from the group consisting of unsubstituted $C_{1-7}$ alkyl; $C_{1-6}$ alkyl substituted with $C_{5-12}$ aryl or $C_{5-12}$ heteroaryl; unsubstituted $C_{2-4}$ alkenyl; unsubstituted $C_{3-10}$ cycloalkyl; $C_{5-12}$ aryl; and $C_{5-12}$ heteroaryl, $R_2$ is unsubstituted $C_{1-7}$ alkyl; $C_{1-6}$ alkyl substituted with $C_{5-12}$ aryl; $C_{5-12}$ heteroaryl; or hydrogen, and $R_3$ is a non-hydrogen substituent selected from the group consisting of unsubstituted $C_{1-7}$ alkyl; $C_{1-6}$ alkyl substituted with $C_{5-12}$ aryl or $C_{5-12}$ heteroaryl; unsubstituted $C_{3-10}$ cycloalkyl; $C_{5-12}$ aryl; and $C_{5-12}$ heteroaryl, the aryl and heteroaryl may be unsubstituted or substituted with at least one non-hydrogen substituent selected from the group consisting of $C_{1-4}$ alkyl, $C_{1-4}$ alkoxy, hydroxyl and halogen. Here, the non-hydrogen substituent for the aryl and heteroaryl may further be substituted with $C_{1-4}$ alkyl, $C_{1-4}$ alkoxy, hydroxyl or halogen, and the aryl or heteroaryl may be selected from the group consisting of phenyl, furanyl, thiophenyl, pyridinyl, benzodioxolyl, and naphtyl.

In one embodiment, the compound of Formula 1 may be N4-butyl-N5-cycloheptyl biguanide; N4-propyl-N5-methyl biguanide; N4-hexyl-N5-methyl biguanide; N4-allyl-N5-methyl biguanide; N4-benzyl-N5-methyl biguanide; N4-(phenethyl)-N5-methyl biguanide; N4-hexyl-N5-(butane-2-yl)biguanide; N4-(phenethyl)-N5-(butane-2-yl)biguanide; N4,N5-dibutyl biguanide; N4-hexyl-N5-butyl biguanide; N4-isopropyl-N5-butyl biguanide; N4-(butane-2-yl)-N5-butyl biguanide; N4-allyl-N5-butyl biguanide; N4-cyclopentyl-N5-butyl biguanide; N4-(furan-2-yl)methyl-N5-butyl biguanide; N4-adamantyl-N5-butyl biguanide; N4-(4-bromo)phenyl-N5-butyl biguanide; N4-benzyl-N5-butyl biguanide; N4-(2-chloro)benzyl-N5-butyl biguanide; N4-(3-chloro)benzyl-N5-butyl biguanide; N4-(4-chloro)benzyl-N5-butyl biguanide; N4-(4-methoxyl)benzyl-N5-butyl biguanide; N4-(3,4-dichloro)benzyl-N5-butyl biguanide; N4-(thiopene-2-yl)ethyl-N5-butyl biguanide; N4-((4-chloro)phenethyl)-N5-butyl biguanide; N4-(pyridine-3-yl)methyl-N5-cyclohexyl biguanide; N4-(phenethyl)-N5-cyclohexyl biguanide; N4-(pyridine-3-yl)methyl-N5-phenyl biguanide; N4-allyl-N5-benzyl biguanide; N4-cyclopentyl-N5-benzyl biguanide; N4-cycloheptyl-N5-benzyl biguanide; N4-(furan-2-yl)methyl-N5-benzyl biguanide; N4-butyl-N5-(phenethyl)biguanide; N4-1-adamantyl-N5-(phenethyl) biguanide; N4-phenyl-N5-(phenethyl)biguanide; N4-(4-chloro)phenyl-N5-(phenethyl) biguanide; N4-(4-trifluoromethyl)phenyl-N5-(phenethyl)biguanide; N4-(furan-2-yl)methyl-N5-(phenethyl)biguanide; N4-(benzo[1,3]dioxol-5-yl)methyl-N5-(phenethyl) biguanide; N4-benzyl-N5-(phenethyl)biguanide; N4-(4-fluoro)benzyl-N5-(phenethyl) biguanide; N4-(thiopene-2-yl)ethyl-N5-(phenethyl)biguanide; N4,N5-di(phenethyl) biguanide; N4-methyl-N5,N5-(benzyl)(methyl)biguanide; N4-butyl-N5,N5-(benzyl)(isopropyl)biguanide; N4-(4-methoxyl)benzyl-N5,N5-(1-naphthylmethyl)(methyl)biguanide; N4-(phenethyl)-N5,N5-(phenethyl)(methyl) biguanide; N4-(phenethyl)-N5,N5-(butyl)(ethyl)biguanide; N4-(phenethyl)-N5,N5-dihexyl biguanide or N4-(phenethyl)-N5,N5-(butyl) (benzyl)biguanide.

Meanwhile, the pharmaceutically acceptable salt of the compound of Formula 1 according to the present invention may be an acid addition salt formed using an organic acid or inorganic acid. Examples of the organic acid include formic acid, acetic acid, propionic acid, lactic acid, butyric acid, isobutyic acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranyl acid, dichloroacetic acid, aminooxy acetic acid, benzensulfonic acid, p-toluenesulfonic acid and methanesulfonic acid, and examples of the inorganic acid include hydrochloric acid, bromic acid, sulfuric acid, phosphoric acid, nitric acid, carbonic acid and boric acid. The above-mentioned acid addition salt may be prepared by a general method of preparing a salt, including a) directly mixing the compound of Formula 1 and an acid, b) dissolving one of the compound and an acid in a solvent or a hydrated solvent and mixing the resulting solution with the other element, or c) dissolving the compound of Formula 1 and an acid in a solvent or a hydrated solvent, respectively, and mixing them.

When the compound of Formula 1 has an acid group such as a carboxyl group and a sulfonic group, the compound may become a zwitterionic salt, and examples of the salt may include alkali metal salts (i.e., a sodium salt, a potassium salt, etc.), alkali earth metal salts (i.e., a calcium salt, a magnesium salt, etc.), inorganic acid-based salts (i.e., an aluminum salt, an ammonium salt, etc.), and basic addition salts (i.e., trimethyl amine, triethyl amine, pyridine, picoline, ethanolamine, diethanolamine, triethanolamine, dicyclohexyl amine, N,N'-dibenzylethylenediamine-based salt, etc.). In addition, the salt of the compound of Formula 1 may be a basic amino acid-based salt (i.e., an arginine, lysine, or ornitine-based salt) or an acidic amino acid-based salt (i.e., an aspartame-based salt).

In one embodiment, the pharmaceutically acceptable salt of the compound of Formula 1 may be a salt with an acid selected from the group consisting of formic acid, acetic acid, propionic acid, lactic acid, butyric acid, isobutyic acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranyl acid, benzensulfonic acid, p-toluenesulfonic acid, methanesulfonic acid, dichloroacetic acid, aminooxy acetic acid, hydrochloric acid, bromic acid, sulfuric acid, phosphoric acid, nitric acid, carbonic acid and boric acid.

The compound of Formula 1 according to the present invention may be prepared by multiple methods.

In one embodiment, a method of preparing the compound of Formula 1 includes reacting a compound of Formula 2 with a compound of Formula 3 in at least one organic solvent in the presence of a base to obtain a compound of Formula 4; and desulfonizing the compound of Formula 4 with a compound of Formula 5 in the presence of a catalyst to obtain the compound of Formula 1.

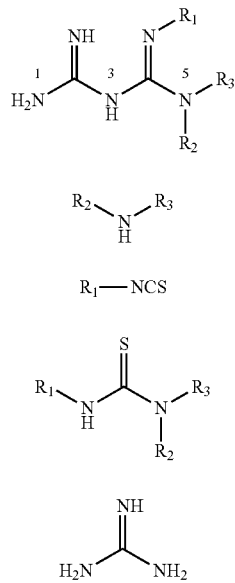

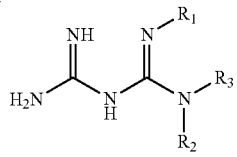

In these formulas, $R_1$, $R_2$, and $R_3$ are the same as defined in Formula 1. Also, NCS in Formula 3 refers to isothiocyanate.

In the preparation method, the base may be selected from, but is not limited to, the group consisting of triethylamine, trimethylamide and diisopropylethylamine, and the organic solvent may be selected from, but is not limited to, the group consisting of dichloromethane, dichloroethane, and dimethylformamide.

Meanwhile, the catalyst used in the desulfurization may be mercury oxide, iodomethane, iodomethane/siver nitride, iodomethane/mercury chloride, peroxide, copper or zinc, and preferably mercury oxide, but the present invention is not limited thereto.

The method may be illustrated in Reaction Scheme 1 and will be described in steps.

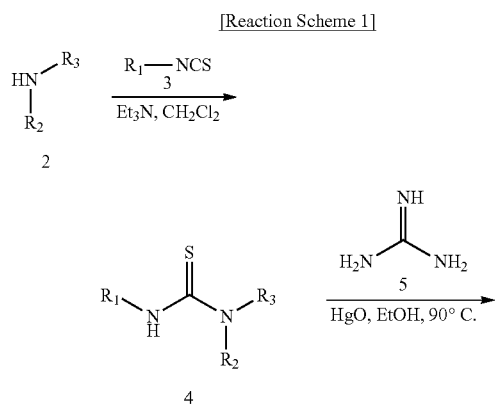

In the method of preparing the compound of Formula 1, the thiourea compound of Formula 4 used as an intermediate may be obtained by reacting the substituted amine of Formula 2 with the compound of Formula 3 in at least one organic solvent in the presence of a base. In addition, the compound of Formula 4 may be desulfonized with the compound of Formula 5 in at least one organic solvent in the presence of a catalyst, thereby obtaining the compound of Formula 1.

As the base used in preparing the thiourea compound of Formula 4, trimethylamine or diisopropylethylamine may be used, and as the organic solvent, dichloromethane, dichloroethane, or dimethylformamide may be used. The reaction temperature is in the range of 0° C. to room temperature.

After the thiourea compound of Formula 4 obtained above is dissolved in at least one organic solvent (i.e., methanol, ethanol, 1,4-dioxane, or dimethylformamide), a catalyst is added, and then the mixture is refluxed with stirring. Here, the amount of the catalyst is approximately 1 to 2 molar equivalents to the compound of Formula 4, the amount of the compound of Formula 5 is approximately 1 to 3 molar equivalents to the compound of Formula 4, and the reaction temperature is in a range of the reflux temperature of the solvent used (i.e., room temperature to 90° C. for ethanol). When the reaction is completed, the resulting product is filtered, and the pH of the reaction solution is controlled to approximately 4 to 5 using an acid, such as hydrochloric acid. A resulting solution is concentrated and purified, thereby yielding the compound of Formula 1 or a pharmaceutically acceptable salt thereof.

Compared to conventional drugs, only a small dose of the compound of Formula 1 or the pharmaceutically acceptable salt thereof obtained as such may exhibit effects of lowering blood sugar and lowering lipid concentration, and thus, may be useful to treat diabetes mellitus, obesity, hyperlipidemia, hypercholesterolemia, fatty liver, coronary artery disease, osteoporosis, polycystic ovarian syndrome, metabolic syndrome, etc.

Another aspect of the present invention provides a drug comprising the compound of Formula 1 or a pharmaceutically acceptable salt thereof as an active ingredient.

Still another aspect of the present invention provides a pharmaceutical composition comprising a compound of Formula 1 or a pharmaceutically acceptable salt thereof as an active ingredient to treat a disease selected from the group consisting of diabetes mellitus, obesity, hyperlipidemia, hypercholesterolemia, fatty liver, coronary artery disease, osteoporosis, polycystic ovarian syndrome, metabolic syndrome, cancer, muscle pain, myocyte damage and rhabdomyolysis, a use of the compound of Formula 1 or the pharmaceutically acceptable salt thereof to treat the above-mentioned disease, and a method of treating the disease including administering a therapeutically effective amount of the compound of Formula 1 or the pharmaceutically acceptable salt thereof to a patient.

In one embodiment, the diabetes mellitus may be non-insulin-dependent diabetes mellitus.

In one embodiment, the cancer may be breast cancer, colorectal cancer, gastric cancer, liver cancer, lung cancer, blood cancer, prostate cancer, brain cancer, pancreatic cancer, ovarian cancer, or endometrial cancer.

The pharmaceutical composition of the present invention comprises at least one pharmaceutically acceptable carrier in addition to an active ingredient. As used in the present invention, "pharmaceutically acceptable carrier" refers to a known pharmaceutically acceptable excipient, which is useful to formulate a pharmaceutically active compound for administration to a patient and is substantially non-toxic and non-irritating under the conditions it is used. An exact ratio of the excipient is determined by standard pharmaceutical practice, as well as solubility, chemical characteristics and selected route of administration of the active compound.

The pharmaceutical composition of the present invention may be formulated in a suitable form for a desired administration method using suitable, physiologically acceptable adjuvants such as an excipient, a disintegrating agent, a sweetening agent, a binder, a coating agent, a swelling agent, a lubricating agent, a glossing agent, a flavoring agent, etc.

The pharmaceutical composition may be formulated in the form of a tablet, a capsule, a pill, a granule, powder, an injection or a liquid, but the present invention is not limited thereto.

Meanwhile, in the present invention, "patient" refers to warm-blooded animals such as mammals with a specific disease, disorder or illness, for example, including humans, orangutans, mice, rats, dogs, cows, chickens, pigs, goats, sheep, etc., but the present invention is not limited thereto.

In addition, "treating" includes relieving a symptom temporarily or permanently, eliminating a cause of the symptom, and preventing or lowering occurrence of the symptom, progression of the disease, disorder or illness, but the present invention is not limited thereto.

An effective amount of the active ingredient of the pharmaceutical composition of the present invention refers to an amount required for treating a disease. Therefore, the effective amount may be controlled by various factors such as type and severity of a disease, kinds and contents of an active ingredient and other ingredients contained in the composition, a type of formulation, age, body weight, general medical conditions, sex and diet of a patient, duration and route of administration, release rate of the composition, treatment regime, and drugs simultaneously used. For example, to a male adult having a body weight of 60 kg, the compound of Formula 1 may be administered once to several times a day in a dosage range from 0.5 to 100 mg/kg of body weight. However, the dosage may vary depending on various factors listed above, and in some cases, a smaller or larger amount than the above-mentioned dosage of the composition may be administered.

Advantageous Effects

A biguanide derivative of Formula 1 according to the present invention can exhibit excellent effects on activation of AMPK and inhibition of cancer cell proliferation in a low dose compared with conventional drugs, and thus, can be useful to treat diabetes mellitus, obesity, hyperlipidemia, hypercholesterolemia, fatty liver, coronary artery disease, osteoporosis, polycystic ovarian syndrome, metabolic syndrome, cancer, etc.

BEST MODE

The advantages and features of the present invention and the method of revealing them will be explicit from the following examples described in detail. However, it is to be distinctly understood that the present invention is not limited thereto but may be otherwise variously embodied and practiced. It is obvious that the following examples are to complete the disclosure of the invention and to indicate the scope of the present invention to a skilled artisan completely, and the present invention will be defined only by the scope of the claims.

EXAMPLES

Example 1

Preparation of N4-butyl-N5-cycloheptyl biguanide hydrochloride

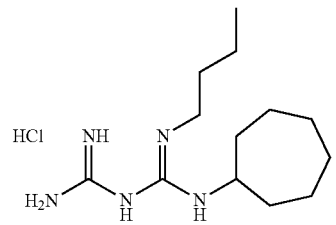 [SMILES: Cl ; CCCC/N=C(/NC(=N)N)NC1CCCCCC1]

(1-1) Synthesis of 1-isothiocyanatobutane

A solution prepared by dissolving carbon sulfide (4.1 ml, 68.3 mmol) in 1,2-dichloroethane (10 ml) was slowly added to a solution prepared by dissolving butyl amine (6.7 ml, 68.3 mmol) in 1,2-dichloroethane (20 ml) at 0° C. for 15 minutes. After trimethylamine (9.53 ml, 68.3 mmol) was added to the mixed reaction solution, and the reaction mixture was stirred at room temperature for 1 hour. Ethyl chloroformate (6.5 ml, 68.3 mmol) was added to the mixed solution and stirred for 2 hours. After confirming completion of the reaction, water (20 ml) was added to the reaction vessel, and 2N of a sodium hydroxide aqueous solution (20 ml) was added. After separating an organic layer, a aqueous layer was extracted over dichloromethane (3×20 ml). The organic layer was washed with brine (10 ml), dried on sodium sulfate anhydrous, filtered and concentrated, thereby obtaining a yellow liquid, 1-isothiocyanatobutane (6.2 g, 78%). The compound was used in the subsequent reaction without a further purification step.

(1-2) Preparation of 1-butyl-3-cycloheptylthiourea

A solution prepared by dissolving 1-isothiocyanatobutane (3.0 ml, 26.0 mmol) in dichloromethane (5 ml) was slowly added to a solution prepared by dissolving 1-cycloheptylamine (3.3 ml, 26.0 mmol) in dichloromethane (20 ml) at 0° C. for 15 minutes. Triethylamine (7.3 ml, 52.1 mmol) was added to the mixed reaction solution and stirred at room temperature for 2 hours. After confirming completion of the reaction, distilled water (10 ml) was added to the reaction solution, and 1N of an HCl aqueous solution was added to neutralize. After separating an organic layer, a aqueous layer was extracted over dichloromethane (3×20 ml), and the organic layer was dried on sodium sulfate anhydrous, filtered and concentrated. The concentrated organic layer was purified by flash column chromatography (hexane:ethylacetate=3:1), thereby obtaining a target compound as a yellow liquid (4.1 g, 68%). The compound was used in the subsequent reaction.

(1-3) Synthesis of N4-butyl-N5-cycloheptyl biguanide hydrochloride

While the compounds (4.1 g, 18.0 mmol) obtained in the previous steps (1-2) were stirred in an ethanol solution (20 ml), mercury oxide (II) (7.8 g, 36.1 mmol) and guanidine hydrochloride (5.2 g, 54.0 mmol) were added. The mixed solution was refluxed with stirring for 12 hours, and the reaction mixture was cooled and filtered using cellite 545. The filtrate was concentrated, and the concentrated filtrate was purified by flash column chromatography (dichloromethane:methanol=9:1). The resulting compound was dissolved in 6N of a methanol hydrochloride solution, and then concentrated under reduced pressure, thereby obtaining a target compound as a white solid (2.0 g, 38%).

$^1$H NMR (600 MHz, DMSO-$d_6$) δ 7.53 (br s, 2H), 6.63 (br s, 3H), 3.54 (m, 1H), 2.99 (t, 2H, J=7.2 Hz), 1.76 (m, 2H), 1.56 (m, 2H), 1.38-1.49 (m, 8H), 1.23-1.37 (m, 4H), 0.83 (t, 3H, J=7.8 Hz); mp 209-210° C.

Thiourea was synthesized by the same method as in Example 1, except that an amine compound corresponding to the target compound was used instead of 1-butyl amine and 1-heptyl amine respectively used in steps (1-1) and (1-2) of Example 1, and target compounds of Examples 2 to 50 were prepared by the same method as step (1-3) of Example 1.

Example 2

N4-propyl-N5-methyl biguanide hydrochloride

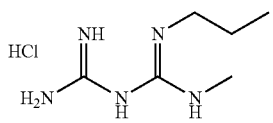

$^1$H NMR (600 MHz, DMSO-$d_6$) δ 7.45 (br s, 2H), 6.70 (br s, 3H), 3.03 (t, 2H, J=6.6 Hz), 2.67 (d, 3H, J=4.2 Hz), 1.46 (m, 2H), 0.85 (t, 3H, J=7.2 Hz); mp 170-171° C.

Example 3

N4-hexyl-N5-methyl biguanide hydrochloride

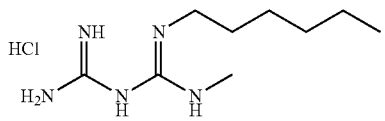

$^1$H NMR (600 MHz, DMSO-$d_6$) δ 7.46 (br s, 2H), 6.72 (br s, 3H), 3.06 (t, 2H, J=6.6 Hz), 2.66 (d, 3H, J=4.2 Hz), 1.44 (m, 2H), 1.22-1.31 (m, 6H), 0.86 (t, 3H, J=7.2 Hz)

Example 4

N4-allyl-N5-methyl biguanide hydrochloride

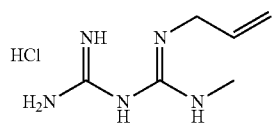

$^1$H NMR (600 MHz, DMSO-$d_6$) δ 7.65 (br s, 1H), 7.42 (d, 1H, J=4.2 Hz), 6.71 (br s, 3H), 5.82 (m, 1H), 5.18 (ddd, 1H, J=16.8, 1.2, 1.2 Hz), 5.09 (ddd, 1H, J=10.2, 1.2, 1.2 Hz), 3.75 (m, 2H), 2.68 (d, 3H, J=4.2 Hz); mp 156-157° C.

Example 5

N4-benzyl-N5-methyl biguanide hydrochloride

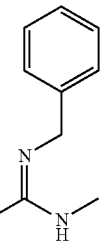
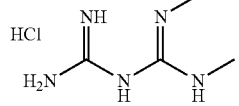

$^1$H NMR (600 MHz, DMSO-$d_6$) δ 7.90 (br s, 1H), 7.51 (d, 1H, J=4.8 Hz), 7.25-7.34 (m, 5H), 6.79 (br s, 3H), 4.35 (d, 2H, J=5.4 Hz), 2.71 (d, 3H, J=4.8 Hz); mp 113-115° C.

Example 6

N4-(phenetyl)-N5-methyl biguanide hydrochloride

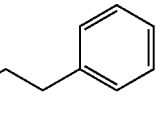
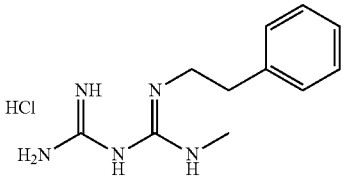 [SMILES: Cl ; CN/C(=N\CCc1ccccc1)NC(=N)N]

$^1$H NMR (600 MHz, DMSO-$d_6$) δ 7.53 (br s, 1H), 7.47 (br s, 1H), 7.30 (m, 3H), 7.22 (m, 3H), 6.74 (br s, 2H), 3.30 (m, 2H), 2.78 (t, 2H, J=7.8 Hz), 2.66 (d, 3H, J=4.8 Hz); mp 126-127° C.

Example 7

N4-hexyl-N5-(butane-2-yl)biguanide hydrochloride

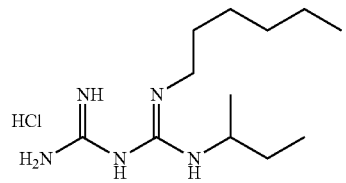 [SMILES: Cl ; CCCCCC/N=C(/NC(=N)N)NC(C)CC]

$^1$H NMR (600 MHz, DMSO-$d_6$) δ7.41 (br s, 1H), 7.24 (br s, 1H), 6.58 (br s, 3H), 3.53 (m, 1H), 3.04 (dt, 2H, J=6.0, 6.0 Hz), 1.43 (m, 4H), 1.27 (m, 6H), 1.07 (d, 3H, J=4.2 Hz), 0.85 (m, 6H); mp 175-176° C.

Example 8

N4-(phenetyl)-N5-(butyl-2-yl)biguanide hydrochloride

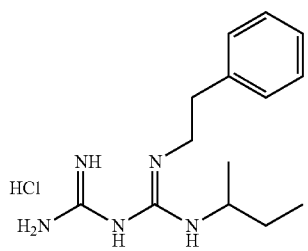 [SMILES: Cl ; CCC(C)N/C(=N\CCc1ccccc1)NC(=N)N]

$^1$H NMR (600 MHz, DMSO-$d_6$) δ 7.49 (br s, 1H), 7.21-7.35 (m, 6H), 6.64 (br s, 3H), 3.53 (m, 1H), 3.30 (m, 2H), 2.80 (t, 2H, J=6.6 Hz), 1.43 (m, 2H), 1.05 (dd, 3H, J=6.6, 2.4 Hz), 0.83 (td, 3H, J=7.8, 2.4 Hz); mp 181-183° C.

Example 9

N4,N5-dibutyl biguanide hydrochloride

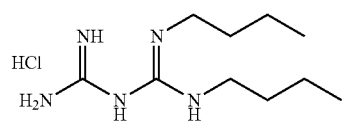

$^1$H NMR (600 MHz, DMSO-$d_6$) δ 3.11 (m, 4H), 1.47 (tt, 4H, J=7.2, 7.2 Hz), 1.30 (m, 4H), 0.88 (t, 6H, J=7.8 Hz); mp 112-114° C.

Example 10

N4-hexyl-N5-butyl biguanide hydrochloride

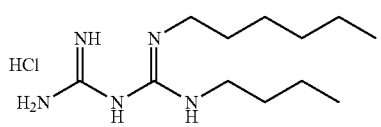 [SMILES: Cl ; CCCCCC/N=C(\NCCCC)NC(=N)N]

$^1$H NMR (600 MHz, DMSO-$d_6$) δ 7.55 (br s, 2H), 6.68 (br s, 3H), 3.04 (m, 4H), 1.44 (m, 4H), 1.23-1.32 (m, 8H), 0.85 (m, 6H)

Example 11

N4-isopropyl-N5-butyl biguanide hydrochloride

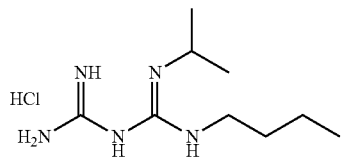

$^1$H NMR (600 MHz, DMSO-$d_6$) δ 7.44 (br s, 1H), 7.34 (d, 1H, J=4.8 Hz), 6.61 (br s, 3H), 3.67 (m, 2H), 3.00 (m, 2H), 1.40 (tt, 2H, J=7.8, 7.8 Hz), 1.25 (m, 2H), 1.05 (d, 6H, J=6.6 Hz), 0.83 (t, 3H, J=7.8 Hz); mp 173-175° C.

Example 12

N4-(butane-2-yl)-N5-butyl biguanide hydrochloride

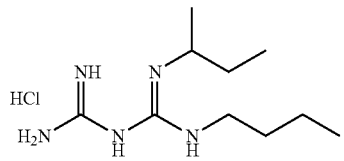

$^1$H NMR (600 MHz, DMSO-$d_6$) δ 7.49 (br s, 1H), 7.34 (br s, 1H), 6.62 (br s, 3H), 3.52 (m, 1H), 3.04 (dt, 2H, J=6.6, 6.6 Hz), 1.44 (m, 4H), 1.29 (m, 2H), 1.06 (d, 3H, J=6.6 Hz), 0.87 (t, 3H, J=7.2 Hz), 0.83 (t, 3H, J=7.8 Hz); mp 193-194° C.

Example 13

N4-allyl-N5-butyl biguanide hydrochloride

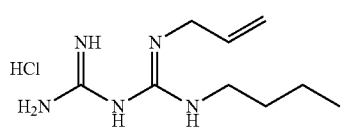

$^1$H NMR (600 MHz, DMSO-$d_6$) δ 7.60 (br s, 1H), 7.49 (br s, 1H), 6.70 (br s, 3H), 5.82 (ddt, 1H, J=17.4, 10.8, 5.4 Hz), 5.18 (dd, 1H, J=17.4, 1.8 Hz), 5.09 (dd, 1H, J=10.8, 1.8 Hz), 3.72 (dd, 2H, J=5.4, 5.4 Hz), 3.06 (dt, 2H, J=7.2, 7.2 Hz), 1.44 (m, 2H), 1.28 (m, 2H), 0.87 (t, 3H, J=7.8 Hz); mp 113-115° C.

Example 14

N4-cyclopentyl-N5-butyl biguanide hydrochloride

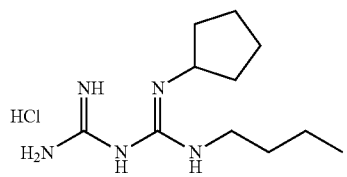 [SMILES: Cl ; CCCCN/C(=N\C1CCCC1)NC(=N)N]

$^1$H NMR (600 MHz, DMSO-d$_6$) δ 7.80 (br s, 2H), 6.88 (br s, 3H), 3.85 (m, 1H), 3.05 (m, 2H), 1.81 (m, 2H), 1.63 (m, 2H), 1.43 (m, 6H), 1.29 (m, 2H), 0.85 (t, 3H, J=6.6 Hz); mp 190-191° C.

Example 15

N4-(furane-2-yl)methyl-N5-butyl biguanide hydrochloride

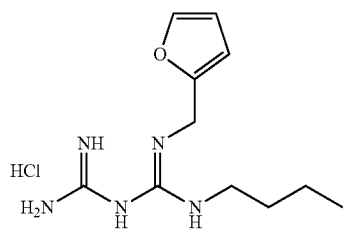 [SMILES: Cl ; CCCCN/C(=N\Cc1ccco1)NC(=N)N]

$^1$H NMR (600 MHz, DMSO-d$_6$) δ 7.68 (br s, 1H), 7.60 (d, 1H, J=1.2 Hz), 7.59 (br s, 1H), 6.81 (br s, 3H), 6.41 (dd, 1H, J=3.3, 1.2 Hz), 6.32 (d, 1H, J=3.3 Hz), 4.30 (d, 2H, J=5.4 Hz), 3.06 (dt, 2H, J=6.6, 6.6 Hz), 1.44 (m, 2H), 1.28 (m, 2H), 0.86 (t, 3H, J=7.8 Hz); mp 113-114° C.

Example 16

N4-adamantyl-N5-butyl biguanide hydrochloride

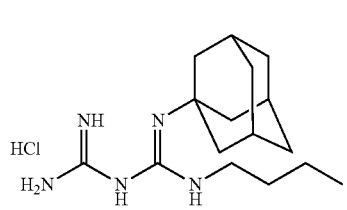 [SMILES: Cl ; CCCCN/C(=N\C12CC3CC(CC(C3)C1)C2)NC(=N)N]

$^1$H NMR (600 MHz, DMSO-d$_6$) δ 7.29 (br s, 1H), 7.10 (br s, 1H), 6.57 (br s, 2H), 3.21 (dt, 2H, J=6.6, 6.6 Hz), 2.08 (m, 2H), 2.06 (m, 2H), 1.93 (m, 5H), 1.50-1.68 (m, 6H), 1.47 (m, 3H), 1.31 (m, 2H), 0.89 (t, 3H, J=7.2 Hz); mp 193-194° C.

Example 17

N4-(4-bromo)phenyl-N5-butyl biguanide hydrochloride

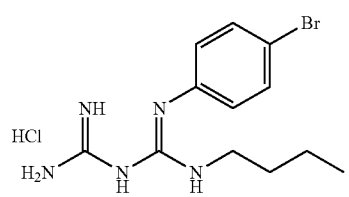 [SMILES: Cl ; CCCCN/C(=N\c1ccc(Br)cc1)NC(=N)N]

$^1$H NMR (600 MHz, DMSO-d$_6$) δ 9.93 (br s, 1H), 7.92 (br s, 1H), 7.47 (d, 2H, J=9.0 Hz), 7.16 (d, 2H, J=9.0 Hz), 7.13 (br s, 3H), 3.13 (dt, 2H, J=6.0, 6.0 Hz), 1.49 (m, 2H), 1.34 (m, 2H), 0.55 (t, 3H, J=7.2 Hz); mp 195-196° C.

Example 18

N4-benzyl-N5-butyl biguanide hydrochloride

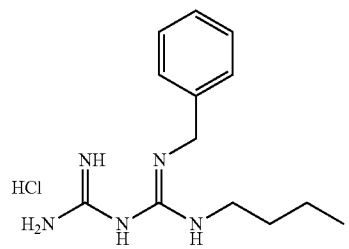 [SMILES: Cl ; CCCCN/C(=N\Cc1ccccc1)NC(=N)N]

$^1$H NMR (600 MHz, DMSO-d$_6$) δ 8.02 (br s, 1H), 7.66 (br s, 1H), 7.24-7.36 (m, 5H), 6.83 (br s, 3H), 4.33 (d, 2H, J=6.6 Hz), 3.08 (m, 2H), 1.45 (m, 2H), 1.28 (m, 2H), 0.86 (t, 3H, J=7.2 Hz)

Example 19

N4-(2-chloro)benzyl-N5-butyl biguanide hydrochloride

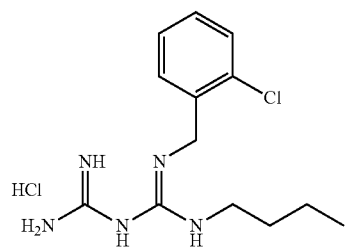 [SMILES: Cl ; CCCCN/C(=N\Cc1ccccc1Cl)NC(=N)N]

$^1$H NMR (600 MHz, DMSO-d$_6$) δ 7.88 (dd, 1H, J=6.0, 4.5 Hz), 7.61 (br s, 1H), 7.44 (dd, 1H, J=7.5, 0.6 Hz), 7.29-7.39 (m, 3H), 6.77 (br s, 3H), 4.40 (d, 2H, J=5.4 Hz), 3.11 (m, 2H), 1.49 (m, 2H), 1.31 (m, 2H), 0.88 (t, 3H, J=7.2 Hz); mp 147-148° C.

Example 20

N4-(3-chloro)benzyl-N5-butyl biguanide hydrochloride

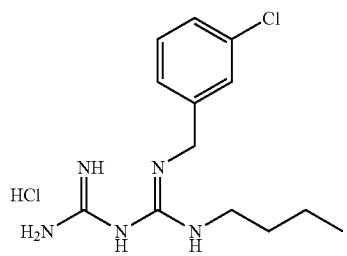 [SMILES: Cl ; CCCCN/C(=N\Cc1cccc(Cl)c1)NC(=N)N]

$^1$H NMR (600 MHz, DMSO-d$_6$) δ 8.02 (br s, 1H), 7.62 (br s, 1H), 7.51 (d, 1H, J=0.6 Hz), 7.30-7.37 (m, 2H), 7.27 (d, 1H, J=7.2 Hz), 6.81 (br s, 3H), 4.34 (s. 2H), 3.09 (t, 2H, J=6.6 Hz), 1.46 (m, 2H), 1.28 (m, 2H), 0.87 (t, 3H, J=7.2 Hz)

Example 21

N4-(4-chloro)benzyl-N5-butyl biguanide hydrochloride

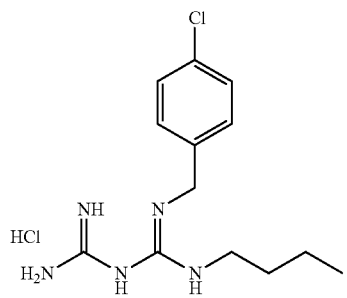 [SMILES: Cl ; CCCCN/C(=N\Cc1ccc(Cl)cc1)NC(=N)N]

$^1$H NMR (600 MHz, DMSO-d$_6$) δ 7.89 (br s, 1H), 7.51 (br s, 1H), 7.36 (d, 2H, J=8.4 Hz), 7.29 (d, 2H, J=8.4 Hz), 6.70 (br s, 3H), 4.27 (d, 2H, J=4.4 Hz), 3.03 (dt, 2H, J=4.4, 4.4 Hz), 1.41 (m, 2H), 1.23 (m, 2H), 0.82 (t, 3H, J=7.2 Hz); mp 113-115° C.

Example 22

N4-(4-methoxyl)benzyl-N5-butyl biguanide hydrochloride

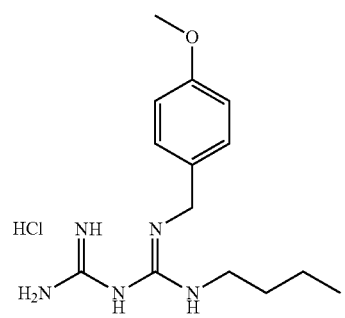 [SMILES: Cl ; CCCCN/C(=N\Cc1ccc(OC)cc1)NC(=N)N]

$^1$H NMR (600 MHz, DMSO-d$_6$) δ 7.25 (d, 2H, J=8.4 Hz), 6.94 (br s, 3H), 6.89 (d, 2H, J=8.4 Hz), 4.27 (d, 2H, J=5.4 Hz), 3.73 (s, 3H), 3.10 (dt, 2H, J=6.6, 6.6 Hz), 1.46 (m, 2H), 1.28 (m, 2H), 0.87 (t, 3H, J=7.2)

Example 23

N4-(3,4-dichloro)benzyl-N5-butyl biguanide hydrochloride

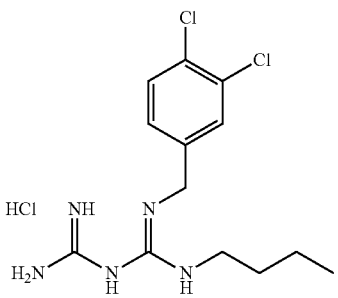 [SMILES: Cl ; CCCCN/C(=N\Cc1ccc(Cl)c(Cl)c1)NC(=N)N]

$^1$H NMR (600 MHz, DMSO-d$_6$) δ 8.08 (br s, 1H), 7.71 (d, 1H, J=1.8 HZ), 7.64 (br s, 1H), 7.39 (dd, 1H, J=7.8, 1.8 HZ), 7.31 (dd, 1H, J=7.8, 1.8 Hz), 6.84 (br s, 3H), 4.33 (s, 2H), 3.09 (t, 2H, J=6.6 Hz), 1.45 (m, 2H), 1.28 (m, 2H), 0.86 (t, 3H, J=7.2 Hz)

Example 24

N4-(thiophene-2-yl)ethyl-N5-butyl biguanide hydrochloride

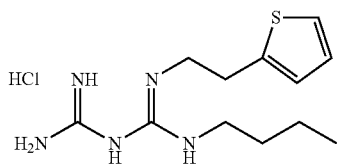 [SMILES: Cl ; CCCCN/C(=N\CCc1cccs1)NC(=N)N]

$^1$H NMR (400 MHz, DMSO-d6) δ 7.48 (t, 1H, J=5.6 Hz), 7.45 (t, 1H, J=4.8 Hz), 7.31 (m, 1H), 6.87-6.93 (m, 2H), 3.28 (m, 2H), 3.03 (m, 2H), 2.97 (t, 2H, J=7.2 Hz), 1.40 (m, 2H), 1.24 (m, 2H), 0.83 (td, 3H, J=7.6, 1.2 HZ); mp 131-133° C.

Example 25

N4-(4-chloro)phenethyl)-N5-butyl biguanide hydrochloride

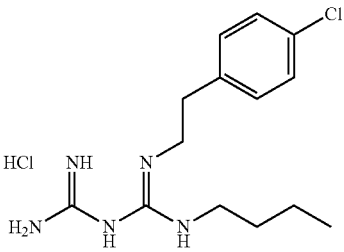 [SMILES: Cl ; CCCCN/C(=N\CCc1ccc(Cl)cc1)NC(=N)N]

¹H NMR (600 MHz, DMSO-d₆) δ 7.52 (m, 2H), 7.51 (d, 2H, J=8.4 Hz), 7.27 (d, 2H, J=8.4 Hz), 6.70 (br s, 3H), 3.28 (m, 2H), 3.04 (m, 2H), 2.78 (t, 2H, J=7.2 Hz), 1.42 (m, 2H), 1.26 (m, 2H), 0.86 (t, 3H, J=7.8 Hz); mp 123-124° C.

Example 26

N4-(pyridine-3-yl)methyl-N5-cyclohexyl biguanide hydrochloride

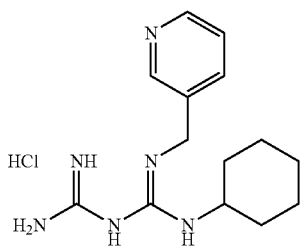 [SMILES: Cl ; N=C(N)N/C(=N/Cc1cccnc1)NC1CCCCC1]

¹H NMR (600 MHz, DMSO-d₆) δ 8.52 (d, 1H, J=4.8 Hz), 8.47 (br s, 1H), 7.92 (m, 1H), 7.87 (br s, 1H), 7.54 (d, 1H, J=7.2 Hz), 7.40 (dd, 1H, J=7.2, 4.8 Hz), 5.39 (s, 2H), 3.88 (m, 1H), 1.70 (m, 4H), 1.57 (m, 1H), 1.04-1.31 (m, 5H); mp 265-266° C.

Example 27

N4-(phenethyl)-N5-cyclohexyl biguanide hydrochloride

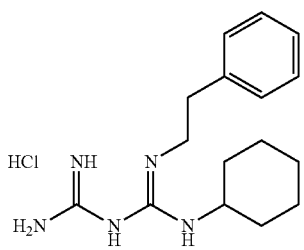 [SMILES: Cl ; N=C(N)N/C(=N/CCc1ccccc1)NC1CCCCC1]

¹H NMR (600 MHz, DMSO-d₆) δ 7.31 (m, 2H), 7.24 (m, 3H), 6.80 (br s, 3H), 3.38 (m, 1H), 3.30 (m, 2H), 2.80 (t, 2H, J=7.8 Hz), 1.79 (m, 2H), 1.68 (m, 2H), 1.55 (m, 1H), 1.10-1.27 (m, 5H); mp 183-184° C.

Example 28

N4-(pyridine-3-yl)methyl-N5-phenyl biguanide hydrochloride

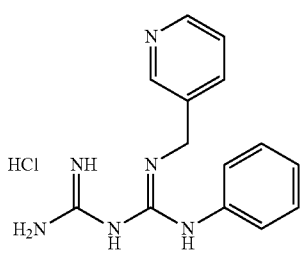 [SMILES: Cl ; N=C(N)N/C(=N/Cc1cccnc1)Nc1ccccc1]

¹H NMR (400 MHz, DMSO-d₆) δ 9.74 (br s, 1H), 8.58 (d, 1H, J=1.6 Hz), 8.50 (dd, 1H, J=5.2, 1.6 Hz), 7.81 (d, 1H, J=7.8 Hz), 7.41 (dd, 1H, J=7.8, 5.2 Hz), 7.31 (m, 2H), 7.00 (m, 3H), 4.57 (s, 2H); mp 189-190° C.

Example 29

N4-allyl-N5-benzyl biguanide hydrochloride

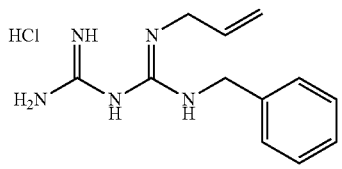 [SMILES: Cl ; C=CC/N=C(\NCc1ccccc1)NC(=N)N]

¹H NMR (600 MHz, DMSO-d₆) δ 8.02 (br s, 1H), 7.76 (br s, 1H), 7.24-7.39 (m, 5H), 6.88 (br s, 3H), 6.83 (m, 1H), 5.19 (d, 1H, J=17.4 Hz), 5.10 (d, 1H, J=10.2 Hz), 4.33 (d, 2H, J=5.4 Hz), 3.76 (m, 2H)

Example 30

N4-cyclopentyl-N5-benzyl biguanide hydrochloride

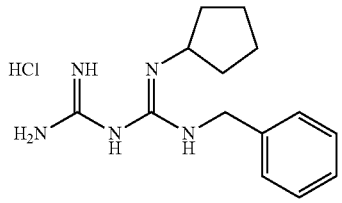 [SMILES: Cl ; N=C(N)N/C(=N/C1CCCC1)NCc1ccccc1]

¹H NMR (600 MHz, DMSO-d₆) δ 7.84 (t, 1H, J=6.0 Hz), 7.55 (d, 1H, J=7.2 Hz), 7.25-7.38 (m, 5H), 6.70 (br s, 3H), 4.33 (d, 2H, J=6.0 Hz), 3.86 (m, 1H), 1.86 (m, 2H), 1.64 (m, 2H), 1.48 (m, 4H); mp 166-167° C.

Example 31

N4-cycloheptyl-N5-benzyl biguanide hydrochloride

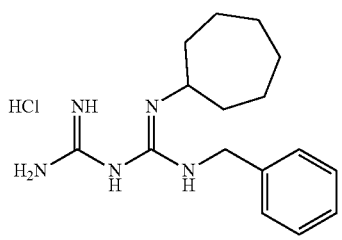 [SMILES: Cl ; N=C(N)N/C(=N/C1CCCCCC1)NCc1ccccc1]

¹H NMR (600 MHz, DMSO-d₆) δ 7.79 (t, 1H, J=5.4 Hz), 7.43 (d, 1H, J=8.4 Hz), 7.25-7.36 (m, 5H), 6.68 (br s, 3H), 4.31 (d, 2H, J=5.4 Hz), 3.60 (m, 1H), 1.83 (m, 2H), 1.60 (m, 2H), 1.46-1.58 (m, 6H), 1.37 (m, 2H); mp 210-202° C.

Example 32

N4-(furan-2-yl)methyl-N5-benzyl biguanide hydrochloride

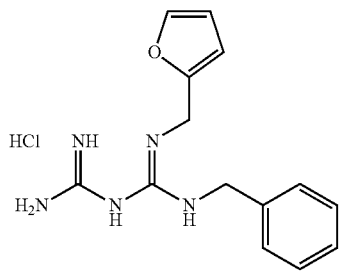 [SMILES: Cl ; N=C(N)N/C(=N/Cc1ccco1)NCc1ccccc1]

$^1$H NMR (600 MHz, DMSO-d$_6$) δ 8.02 (br s, 1H), 7.93 (br s, 1H), 7.61 (d, 1H, J=1.8 Hz), 7.25-7.39 (m, 5H), 6.91 (br s, 3H), 6.42 (dd, 1H, J=2.4, 1.8 Hz), 6.32 (d, 1H, J=2.4 Hz), 4.35 (s, 4H); mp 116-117° C.

Example 33

N4-butyl-N5-(phenethyl)biguanide hydrochloride

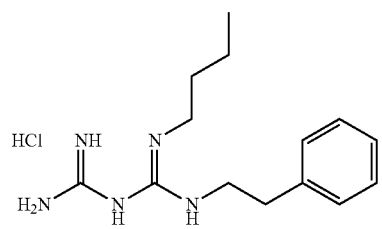 [SMILES: Cl ; CCCC/N=C(\NCCc1ccccc1)NC(=N)N]

$^1$H NMR (600 MHz, DMSO-d$_6$) δ 7.46 (t, 1H, J=4.8 Hz), 7.44 (t, 1H, J=4.8 Hz), 7.26 (m, 2H), 7.19 (m, 3H), 6.62 (br s, 3H), 3.25 (m, 2H), 3.01 (m, 2H), 2.75 (t, 2H, J=7.8 Hz), 1.39 (m, 2H), 1.23 (m, 2H), 0.83 (t, 3H, J=7.2 Hz); mp 178-179° C.

Example 34

N4-adamantyl-N5-(phenethyl)biguanide hydrochloride

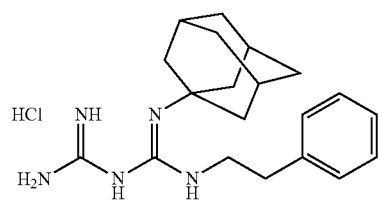 [SMILES: Cl ; N=C(N)N/C(=N/C12CC3CC(CC(C3)C1)C2)NCCc1ccccc1]

$^1$H NMR (600 MHz, DMSO-d$_6$) δ 7.20-7.35 (m, 5H), 7.14 (br s, 1H), 6.58 (br s, 3H), 3.20 (m, 2H), 2.78 (t, 2H, J=7.2 Hz), 1.82-2.01 (m, 9H), 1.56-1.68 (m, 6H); mp 251-252° C.

Example 35

N4-phenyl-N5-(phenethyl)biguanide hydrochloride

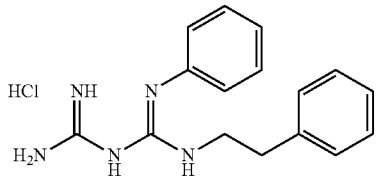 [SMILES: Cl ; N=C(N)N/C(=N/c1ccccc1)NCCc1ccccc1]

$^1$H NMR (600 MHz, DMSO-d$_6$) δ 7.65 (br s, 1H), 7.23-7.38 (m, 6H), 7.16 (m, 2H), 7.09 (m, 1H), 7.06 (br s, 2H), 3.38 (m, 2H), 2.85 (t, 2H, J=7.2 Hz); mp 232-233° C.

Example 36

N4-(4-chloro)phenyl-N5-(phenethyl)biguanide hydrochloride

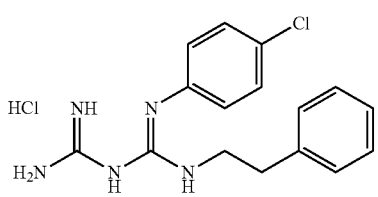 [SMILES: Cl ; N=C(N)N/C(=N/c1ccc(Cl)cc1)NCCc1ccccc1]

$^1$H NMR (600 MHz, DMSO-d$_6$) δ 7.19-7.35 (m, 10H), 6.94 (br s, 3H), 3.41 (m, 2H), 2.83 (t, 2H, J=7.2 Hz); mp 115-116° C.

Example 37

N4-(4-trifluoromethyl)phenyl-N5-(phenethyl)biguanide hydrochloride

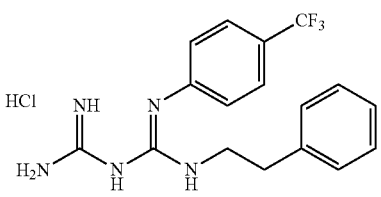 [SMILES: Cl ; N=C(N)N/C(=N/c1ccc(C(F)(F)F)cc1)NCCc1ccccc1]

$^1$H NMR (600 MHz, DMSO-d$_6$) δ 8.06 (br s, 1H), 8.04 (d, 2H, J=8.4 Hz), 7.75 (d, 2H, J=8.4 Hz), 7.20-7.34 (m, 5H), 7.10 (t, 1H, J=5.4 Hz), 6.69 (br s, 2H), 3.31 (m, 2H), 2.70 (t, 2H, J=7.2 Hz); mp 150-151° C.

Example 38

N4-(furan-2-yl)methyl-N5-(phenethyl)biguanide hydrochloride

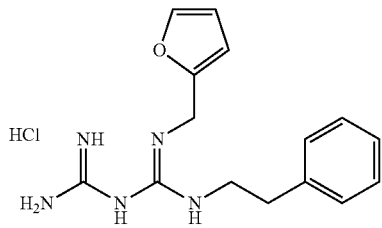 [SMILES: Cl ; N=C(N)N/C(=N/Cc1ccco1)NCCc1ccccc1]

$^1$H NMR (600 MHz, DMSO-$d_6$) δ 7.88 (br s, 1H), 7.62 (br s, 1H), 7.60 (m, 1H), 7.21-7.32 (m, 5H), 6.83 (br s, 3H), 6.42 (m, 1H), 6.31 (m, 1H), 4.32 (s, 2H), 3.31 (m, 2H), 2.80 (t, 2H, J=7.2 Hz)

Example 39

N4-(benzo[1,3]dioxol-5-yl)methyl-N5-(phenethyl)biguanide hydrochloride

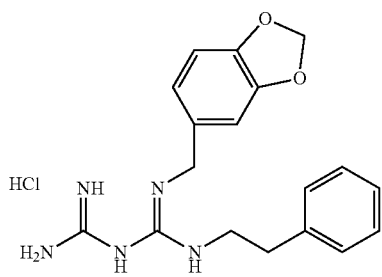 [SMILES: Cl ; N=C(N)N/C(=N/Cc1ccc2c(c1)OCO2)NCCc1ccccc1]

$^1$H NMR (600 MHz, DMSO-$d_6$) δ 7.84 (br s, 1H), 7.54 (br s, 1H), 7.21-7.32 (m, 5H), 6.85-6.89 (m, 2H), 6.75 (m, 4H), 5.99 (s, 2H), 4.22 (s, 2H), 3.32 (m, 2H), 2.79 (t, 2H, J=7.2 Hz); mp 168-169° C.

Example 40

N4-benzyl-N5-(phenethyl)biguanide hydrochloride

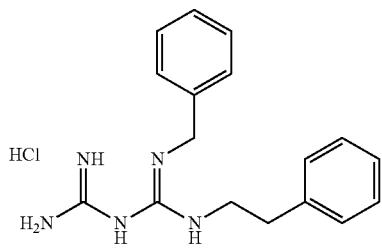 [SMILES: Cl ; N=C(N)N/C(=N/Cc1ccccc1)NCCc1ccccc1]

$^1$H NMR (600 MHz, DMSO-$d_6$) δ 7.87 (t, 1H, J=6.0 Hz), 7.53 (t, 1H, J=5.4 Hz), 7.17-7.31 (m, 10H), 6.71 (br s, 3H), 4.29 (2H, J=6.0 Hz), 3.29 (m, 2H), 2.77 (t, 2H, J=7.8 Hz); mp 165-166° C.

Example 41

N4-(4-fluoro)benzyl-N5-(phenethyl)biguanide hydrochloride

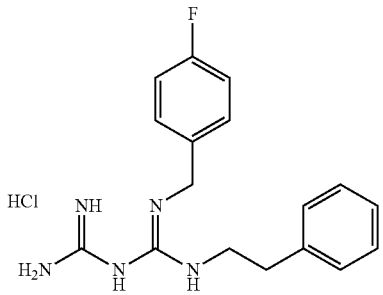 [SMILES: Cl ; N=C(N)N/C(=N/Cc1ccc(F)cc1)NCCc1ccccc1]

$^1$H NMR (600 MHz, DMSO-$d_6$) δ 7.96 (t, 1H, J=6.0 Hz), 7.62 (t, 1H, J=5.4 Hz), 7.10-7.34 (m, 9H), 6.80 (br s, 3H), 4.31 (d, 2H, J=5.4 Hz), 3.31 (m, 2H), 2.81 (t, 2H, J=7.2 Hz); mp 125-127°

Example 42

N4-(thiophene-2-yl)ethyl-N5-(phenethyl)biguanide hydrochloride

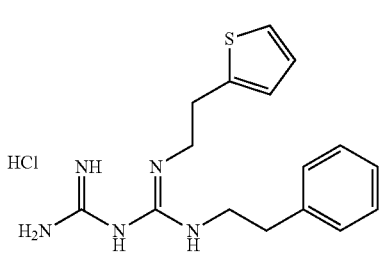 [SMILES: Cl ; N=C(N)N/C(=N/CCc1cccs1)NCCc1ccccc1]

$^1$H NMR (600 MHz, DMSO-$d_6$) δ 7.56 (br s, 2H), 7.36 (dd, 1H, J=5.4, 0.6 Hz), 7.21-7.32 (m, 5H), 6.97 (dd, 1H, J=5.4, 3.6 Hz), 6.90 (d, 1H, J=3.6 Hz), 6.73 (br s, 3H), 3.28-3.42 (m, 4H), 3.00 (t, 2H, J=7.2 Hz), 2.79 (t, 2H, J=7.8 Hz); mp 183-185° C.

Example 43

N4-N5-di(phenethyl)biguanide hydrochloride

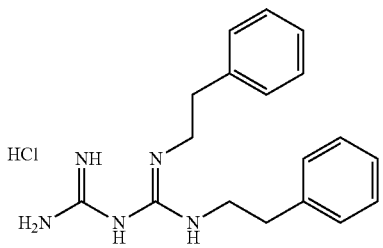 [SMILES: Cl ; N=C(N)N/C(=N/CCc1ccccc1)NCCc1ccccc1]

$^1$H NMR (600 MHz, DMSO-$d_6$) δ 7.47 (t, 1H, J=5.4 Hz), 7.15-7.28 (m, 5H), 6.64 (br s, 1H), 3.25 (m, 2H), 2.73 (t, 2H, J=7.2 Hz); mp 183-184° C.

Example 44

N4-methyl-N5,N5-(benzyl)(methyl)biguanide hydrochloride

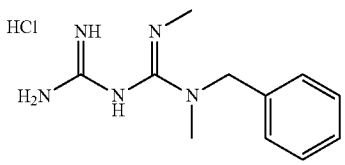 [SMILES: Cl ; C/N=C(/NC(=N)N)N(C)Cc1ccccc1]

¹H NMR (600 MHz, DMSO-d₆) δ 7.78 (q, 1H, J=4.2 Hz), 7.26-7.38 (m, 5H), 6.66 (br, 3H), 4.51 (s, 2H), 2.84 (s, 3H), 2.73 (d, 3H, J=4.2 Hz); mp 120-122° C.

Example 45

N4-butyl-N5,N5-(benzyl)(isopropyl)biguanide hydrochloride

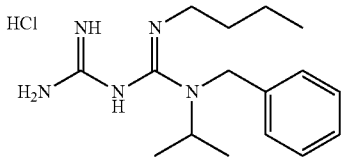 [SMILES: Cl ; CCCC/N=C(/NC(=N)N)N(Cc1ccccc1)C(C)C]

¹H NMR (600 MHz, DMSO-d₆) δ 7.60 (br s, 1H), 7.23-7.34 (m, 5H), 6.67 (br s, 3H), 4.58 (s, 2H), 4.45 (m, 1H) 2.99 (m, 2H), 1.33 (m, 2H), 1.09 (d, 6H, J=6.6 Hz), 1.06 (m, 2H), 0.77 (t, 3H, J=7.8 Hz); mp 170-171° C.

Example 46

N4-(4-methoxyl)benzyl-N5,N5-(1-naphthylmethyl)-(methyl) biguanide hydrochloride

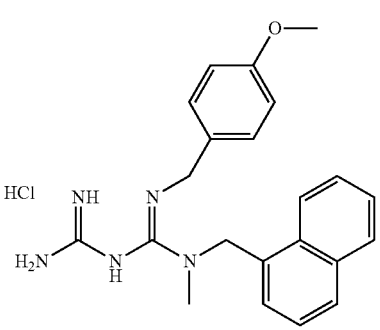 [SMILES: Cl ; COc1ccc(C/N=C(/NC(=N)N)N(C)Cc2cccc3ccccc23)cc1]

¹H NMR (600 MHz, DMSO-d₆) δ 8.29 (br s, 1H), 7.94 (d, 1H. J=7.8 Hz) 7.87 (d, 2H, J=7.8 Hz), 7.52 (m, 2H), 7.47 (dd, 1H, J=7.8, 7.2 Hz), 7.33 (d, 2H, J=7.2 Hz), 7.22 (d, 2H, J=7.8 Hz), 6.86 (d, 2H, J=7.8 Hz), 6.82 (br s, 3H), 4.93 (s, 2H), 4.26 (d, 2H, J=6.0 Hz), 3.70 (s, 3H), 2.83 (s, 3H); mp 125-127° C.

Example 47

N4-(phenethyl)-N5,N5-(phenethyl)(methyl)biguanide hydrochloride

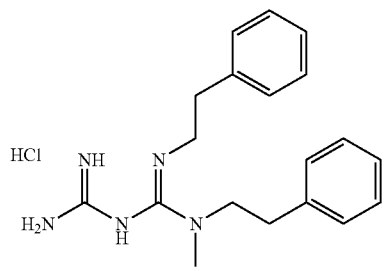 [SMILES: Cl ; CN(CCc1ccccc1)/C(=N\CCc1ccccc1)NC(=N)N]

¹H NMR (600 MHz, DMSO-d₆) δ 7.67 (br s, 1H), 7.17-7.28 (m, 10H), 6.56 (br s, 3H), 3.42 (t, 2H, J=7.2 Hz), 3.22 (m, 2H), 2.83 (s, 3H), 2.76 (m, 4H); mp 144-145° C.

Example 48

N4-(phenethyl)-N5,N5-(butyl)(ethyl)biguanide hydrochloride

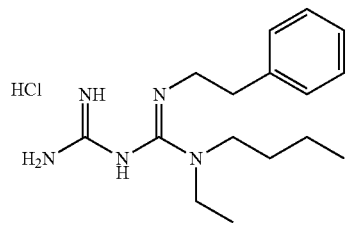 [SMILES: Cl ; CCCCN(CC)/C(=N\CCc1ccccc1)NC(=N)N]

¹H NMR (600 MHz, DMSO-d₆) δ 7.53 (br s, 1H), 7.20-7.31 (m, 5H), 6.50 (br s, 3H), 3.31 (dt, 2H, J=7.2, 7.2 Hz), 3.23 (m, 4H), 2.83 (t, 2H, J=7.2 Hz), 1.43 (m, 2H), 1.23 (m, 2H), 1.04 (t, 3H, J=7.8 Hz), 0.87 (t, 3H, J=7.2 Hz); mp 228-229° C.

Example 49

N4-(phenethyl)-N5,N5-dihexyl biguanide hydrochloride

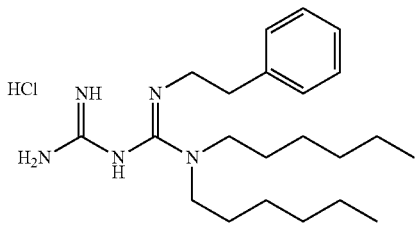 [SMILES: Cl ; CCCCCCN(CCCCCC)/C(=N\CCc1ccccc1)NC(=N)N]

¹H NMR (600 MHz, DMSO-d₆) δ 7.51 (br s, 1H), 7.15-7.26 (m, 5H), 6.50 (br s, 3H), 3.17-3.21 (m, 6H), 2.79

(t, 2H, J=7.2 Hz), 1.39 (m, 4H), 1.14-1.25 (m, 12H), 0.82 (t, 6H, J=7.2 Hz); mp 138-140° C.

Example 50

N4-(phenethyl)-N5,N5-(butyl)(benzyl)biguanide hydrochloride

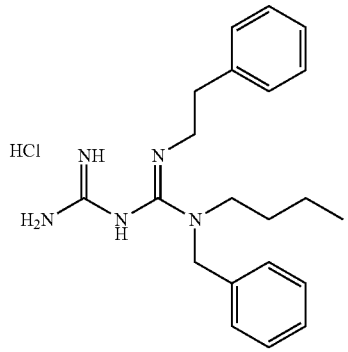 [SMILES: Cl ; CCCCN(Cc1ccccc1)/C(=N\CCc1ccccc1)NC(=N)N]

$^1$H NMR (600 MHz, DMSO-$d_6$) δ 7.69-7.71 (br s, 1H), 7.19-7.36 (m, 10H), 6.67 (br s, 3H), 4.55 (s, 2H), 3.29 (m, 2H), 3.17 (t, 2H, J=7.8 Hz), 2.83 (t, 2H, J=7.2 Hz), 1.37 (m, 2H), 1.16 (m, 2H), 0.80 (t, 3H, J=7.8 Hz); mp 184-185° C.

EXPERIMENTAL EXAMPLES

The effects on inhibition of cancer cell proliferation and activation of AMPK of the compounds synthesized by the method described in the examples of the present invention were evaluated according to the following Experimental Examples.

Experimental Example 1

Measurement of Effect on Inhibition of Cancer Cell Proliferation

HCT116 cells derived from human colorectal cancer were used, and a cancer cell proliferation inhibition effect of a biguanide derivative was confirmed by measuring a concentration value (cell growth inhibition concentration, GIC50) at which cell growth was inhibited 50% using a 3-(4,5-dimethylthiazol-2-yl)-2,5-diphenyltetrazolium bromide (MTT) reagent.

First, the HCT116 cells were put on a 96-well plate and incubated for 24 hours to each have cell count of approximately 5000 in a DMEM medium containing 10% fetal bovine serum. Subsequently, to obtain the GIC50 value of each compound, 100 μM (or 200 μM), 25 μM, 6.25 μM, 1.56 μM or 0.39 μM of the compound was treated to each culture medium and then incubated for 48 hours. To confirm living cells after treatment with the compound, MTT was added to each culture medium and further incubated for 3 hours. Generated formazane crystal was dissolved using dimethyl sulfoxide (DMSO), and absorbance of the solution was measured at 560 nm. After the 48-hour incubation, a ratio of a cell count cultured on a well plate not administered with the compound to a cell count present on the well plate administered with compounds synthesized in the examples was indicated as cell viability (%) according to each administered concentration. A cell viability curve was plotted using the cell viability (%) and the calculated concentration value (GIC50) of the compound, at which 50% of the growth was inhibited, to confirm an effect on the inhibition of cancer cell proliferation.

Results of effects on cancer cell growth inhibition are shown in Table 1.

TABLE 1

| Examples | GIC50 (uM) @ HCT116 |
| --- | --- |
| Metformin HCl | 2172 |
| 1 | >200 |
| 2 | >100 |
| 3 | >100 |
| 4 | >100 |
| 5 | >100 |
| 6 | >100 |
| 7 | >100 |
| 8 | >100 |
| 9 | >100 |
| 10 | 30.3 |
| 11 | >100 |
| 12 | >200 |
| 13 | >200 |
| 14 | >100 |
| 15 | >200 |
| 16 | 34.7 |
| 17 | 126.3 |
| 18 | >200 |
| 19 | >100 |
| 20 | 54.1 |
| 21 | 13.5 |
| 22 | >100 |
| 23 | 35.3 |
| 24 | >100 |
| 25 | 26.5 |
| 26 | >100 |
| 27 | >100 |
| 28 | >100 |
| 29 | >200 |
| 30 | >200 |
| 31 | >100 |
| 32 | >100 |
| 33 | 6.5 |
| 34 | 18.7 |
| 35 | 104.7 |
| 36 | 9.3 |
| 37 | 12.4 |
| 38 | >100 |
| 39 | >100 |
| 40 | 85.6 |
| 41 | 42.8 |
| 42 | 76.0 |
| 43 | 70.2 |
| 44 | >100 |
| 45 | >100 |
| 46 | 99.1 |
| 47 | >100 |
| 48 | >100 |
| 49 | >100 |
| 50 | 59.1 |

Experimental Example 2

Measurement of Effect on AMPK Activation

MCF7 cells derived from human breast cancer cells were used, and an effect of a biguanide derivative on AMPK activation was confirmed using an AMPKα immunoassay kit (Invitrogen, catalog No. KH00651).

The MCF7 cells were put on a 6-well plate and incubated in a DMEM medium containing 10% fetal bovine serum in an incubator to which 5% $CO_2$ was supplied to have a cell count of approximately 5×10$^5$. 50 μM of the derivatives synthesized in the examples were treated to the each culture medium, and the cells were incubated for 24 hours. Subsequently, the cells were lysed by a method presented in the operation manual of the AMPKα immunoassay kit, and 20 μg of cell lysates were yielded through protein assay. A degree of phosphorylation of an AMPKα threonine $172^{nd}$ residue (Thr172) from the cell lysates was confirmed according to a method presented in the operation manual of the AMPKα immunoassay kit to thereby obtain results. A degree of the AMPK activation by biguanide derivatives was exhibited as a degree of phosphorylated AMPKα in the cells cultured in the presence of the compounds synthesized in the examples based on phosphorylated AMPKα in cells cultured without administering the biguanide derivative.

In addition, an experiment was performed in the same manner as described in Experimental Example 2 using metformin as a control group, and the results of the effect on AMPK activation were compared with the effect on AMPK activation when 1 mM metformin was administered.

The results are shown in Table 2.

TABLE 2

| Examples | AMPK Activation | | |
|---|---|---|---|
| | 0 | 50 uM | Fold |
| Metformin HCl | 6.8 | 21.5 (@ 1 mM) | 3.2 |
| 1 | 5.3 | 21.1 | 4.0 |
| 2 | 6.8 | 6.5 | 1.0 |
| 3 | 6.8 | 35.5 | 5.2 |
| 4 | 6.8 | 5.3 | 0.8 |
| 5 | 6.8 | 10.8 | 1.6 |
| 6 | 6.8 | 33.1 | 4.9 |
| 7 | 6.8 | 39.5 | 5.8 |
| 8 | 6.8 | 18.4 | 2.7 |
| 9 | 6.8 | 25.6 | 3.8 |
| 10 | 5.3 | 38.1 | 7.2 |
| 11 | 6.8 | 4.2 | 0.6 |
| 12 | 5.3 | 8.1 | 1.5 |
| 13 | 5.3 | 20.5 | 3.9 |
| 14 | 6.8 | 23.2 | 3.4 |
| 15 | 5.3 | 19.4 | 3.7 |
| 16 | 5.3 | 35.3 | 6.7 |
| 17 | 6.8 | 26.3 | 3.9 |
| 18 | 5.3 | 9.6 | 1.8 |
| 19 | 6.8 | 19.1 | 2.8 |
| 20 | 4.9 | 7.2 | 1.5 |
| 21 | | N.D | |
| 22 | 6.8 | 29.9 | 4.4 |
| 23 | 2.5 | 19.5 | 7.8 |
| 24 | 6.8 | 29.9 | 4.4 |
| 25 | 2.5 | 16.7 | 6.7 |
| 26 | 6.8 | 15.4 | 2.3 |
| 27 | 6.8 | 18.7 | 2.7 |
| 28 | 6.8 | 6.7 | 1.0 |
| 29 | 5.3 | 5.5 | 1.0 |
| 30 | 5.3 | 7.3 | 1.4 |
| 31 | 6.8 | 44.6 | 6.6 |
| 32 | 6.8 | 16.9 | 2.5 |
| 33 | | N.D | |
| 34 | 2.5 | 20.8 | 8.3 |
| 35 | 6.8 | 9.0 | 1.3 |
| 36 | | N.D | |
| 37 | 2.5 | 10.2 | 4.1 |
| 38 | 6.8 | 22.0 | 3.2 |
| 39 | 6.8 | 6.4 | 0.9 |
| 40 | 5.3 | 20.5 | 3.9 |
| 41 | 2.5 | 10.1 | 4.0 |
| 42 | 5.3 | 31.5 | 5.9 |
| 43 | 5.3 | 23.8 | 4.5 |
| 44 | 6.8 | 12.8 | 1.9 |
| 45 | 6.8 | 7.1 | 1.0 |
| 46 | 5.3 | 19.5 | 3.7 |
| 47 | 6.8 | 7.2 | 1.1 |
| 48 | 6.8 | 6.6 | 1.0 |

TABLE 2-continued

| Examples | AMPK Activation | | |
|---|---|---|---|
| | 0 | 50 uM | Fold |
| 49 | 6.8 | 35.2 | 5.2 |
| 50 | 5.3 | 21.4 | 4.0 |

Consequently, it was seen that the derivatives synthesized in the examples effectively inhibited the viability of cancer cells, particularly, colorectal cancer cells, in terms of the effect on cancer cell proliferation inhibition. In addition, it could be observed that the compounds exhibiting a greater effect on AMPK activation at a concentration 20 times lower than the control group, metformin, may have an effect at least 20 times greater than the control group.

The invention claimed is:

1. A method of treating colorectal cancer or breast cancer, comprising:
administering to a patient in need thereof, a pharmaceutical composition comprising a therapeutically effective amount of a compound of Formula 1 or a pharmaceutically acceptable salt thereof of [Formula 1]

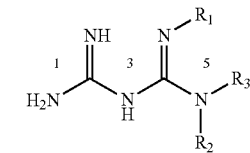

wherein, $R_1$ is a non-hydrogen substituent selected from the group consisting of $C_{1-6}$ alkyl substituted with phenyl; $C_{1-6}$ alkyl substituted with $C_{5-12}$ heteroaryl wherein $C_{5-12}$ heteroaryl is selected from the group consisting of furanyl and pyridinyl; phenyl unsubstituted or substituted with halogen or $C_{1-4}$ alkyl substituted with halogen, and unsubstituted $C_{3-10}$ cycloalkyl;
wherein the phenyl of $C_{1-6}$ alkyl substituted with phenyl is unsubstituted or substituted with at least one non-hydrogen substituent selected from the group consisting of $C_{1-4}$ alkoxy and halogen,
$R_2$ is unsubstituted $C_{1-7}$ alkyl or hydrogen; and
$R_3$ is $C_{1-6}$ alkyl substituted with phenyl or naphthyl;
or the compound of Formula 1 is N4-methyl-N5,N5-(benzyl)(methyl) biguanide.

2. The method of claim 1, wherein the compound of Formula 1 is N4-cyclopentyl-N5-benzyl biguanide; N4-cycloheptyl-N5-benzyl biguanide; N4-(furan-2-yl)methyl-N5-benzyl biguanide; N4-1-adamantyl-N5-(phenethyl) biguanide; N4-phenyl-N5-(phenethyl) biguanide; N4-(4-chloro)phenyl-N5-(phenethyl) biguanide; N4-(4-trifluoromethyl)phenyl-N5-(phenethyl) biguanide; N4-(furan-2-yl)methyl-N5-(phenethyl) biguanide; N4-benzyl-N5-(phenethyl) biguanide; N4-(4-fluoro)benzyl-N5-(phenethyl) biguanide; N4,N5-di(phenethyl) biguanide; N4-methyl-N5,N5-(benzyl)(methyl) biguanide; N4-(4-methoxy)benzyl-N5-(1-naphthylmethyl)(methyl) biguanide; or N4-(phenethyl)-N5,N5-(phenethyl) (methyl) biguanide.

3. The method of claim 1, wherein the pharmaceutically acceptable salt is a salt with an acid selected from the group consisting of formic acid, acetic acid, propionic acid, lactic acid, butyric acid, isobutyic acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranyl acid, benzensulfonic acid, p-toluenesulfonic acid, methanesulfonic acid, dichloroacetic acid, aminooxy acetic acid, hydrochloric acid, bromic acid, sulfuric acid, phosphoric acid, nitric acid, carbonic acid and boric acid.

* * * * *